United States Patent [19]

Deniega

[11] Patent Number: 5,399,167
[45] Date of Patent: Mar. 21, 1995

[54] SAFETY TROCAR

[75] Inventor: Jose C. Deniega, Flemington, N.J.

[73] Assignee: Ethicon, Inc., Somerville, N.J.

[21] Appl. No.: 66,953

[22] Filed: May 24, 1993

Related U.S. Application Data

[60] Division of Ser. No. 700,787, May 15, 1991, Pat. No. 5,215,526, which is a continuation of Ser. No. 371,953, Jun. 27, 1989, Pat. No. 5,066,288.

[30] Foreign Application Priority Data

Jul. 6, 1988 [GB] United Kingdom ............... 8816033

[51] Int. Cl.⁶ ......................................... A61M 5/178
[52] U.S. Cl. .................................. 604/164; 604/171; 604/264; 604/274; 606/185; 128/754
[58] Field of Search .............. 606/167, 170, 172, 182, 606/185; 128/754; 604/51, 117, 136, 157, 164, 165, 166, 167, 170, 171, 264, 268, 272, 273, 274, 209–211

[56] References Cited

U.S. PATENT DOCUMENTS

| | | | |
|---|---|---|---|
| 201,443 | 3/1878 | Parker | 604/209 |
| 2,221,739 | 11/1940 | Reiter | 604/210 |
| 2,295,849 | 9/1942 | Kayden | 604/210 |
| 4,411,653 | 10/1983 | Razi | 606/185 |
| 4,535,773 | 8/1985 | Yoon | 604/169 |
| 4,601,710 | 7/1986 | Moll | 604/165 |
| 4,650,030 | 3/1987 | Moll et al. | 604/165 |
| 4,654,030 | 3/1987 | Moll et al. | 604/165 |
| 4,668,220 | 5/1987 | Hawrylenko | 604/209 |
| 4,710,178 | 12/1987 | Leonard et al. | 604/209 |
| 4,902,280 | 2/1990 | Lander | 604/165 |
| 4,931,042 | 6/1990 | Holmes et al. | 606/185 |
| 5,030,206 | 7/1991 | Lander | 606/185 |

FOREIGN PATENT DOCUMENTS

89/03661  5/1989  WIPO.

*Primary Examiner*—C. Fred Rosenbaum
*Assistant Examiner*—Ronald K. Stright, Jr.
*Attorney, Agent, or Firm*—Paul A. Coletti

[57] ABSTRACT

A safety trocar is provided which includes a spring-loaded shield that shields the cutting tip of the obturator after the obturator penetrates tissue. The distal end of the shield is hemispheric in profile and contains a slot which conforms to the geometry of the cutting tip. The rounded distal end enables the shield to spring forward to shield the cutting tip as soon as the tip perforates the tissue. A valve is located at the proximal end of the trocar tube to seal the end of the tube. The valve is oriented at an acute angle with respect to the longitudinal axis of the trocar tube. The valve is controllable by an external lever which will hold the valve open or permit it to spring shut. An incremental advancement mechanism cooperates with the obturator to permit only incremental advance of the obturator. Instead of using a discrete shield component the shielding function may be provided by spring-loading the trocar tube itself to spring forward and shield the obturator tip after the tip penetrates tissue.

1 Claim, 12 Drawing Sheets

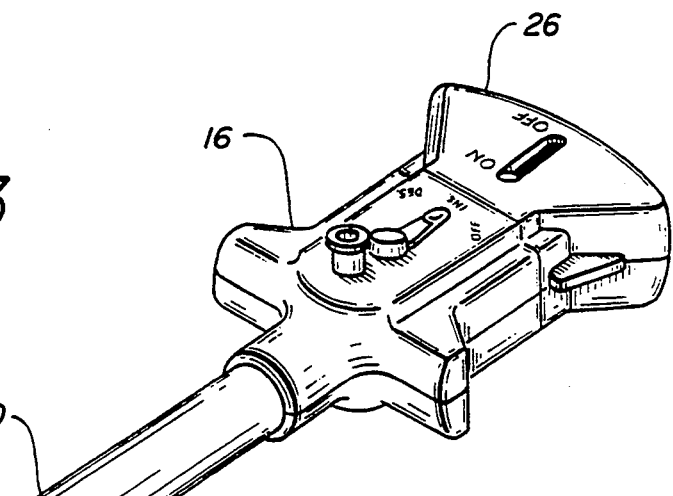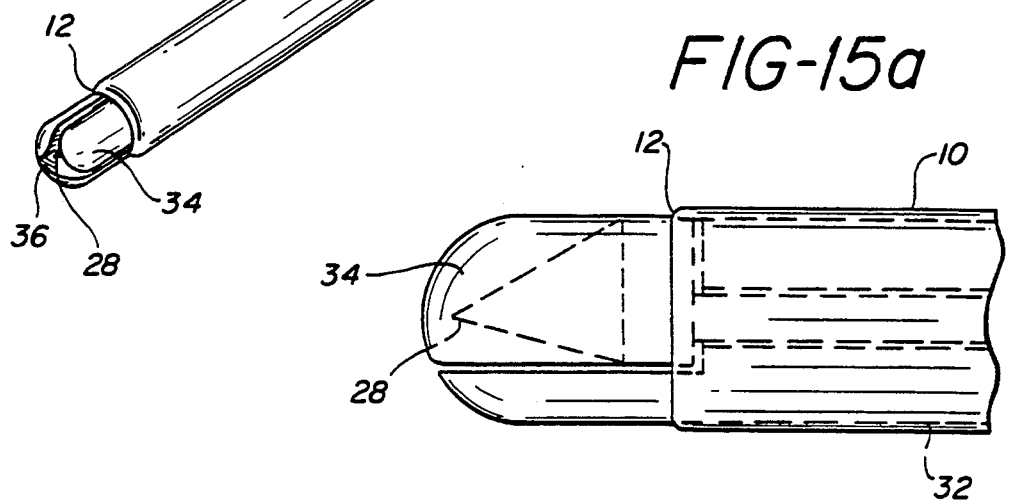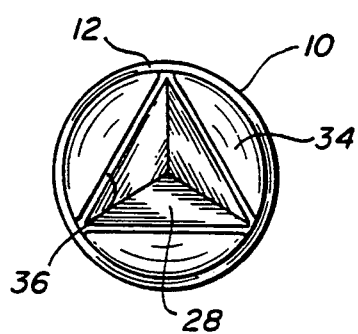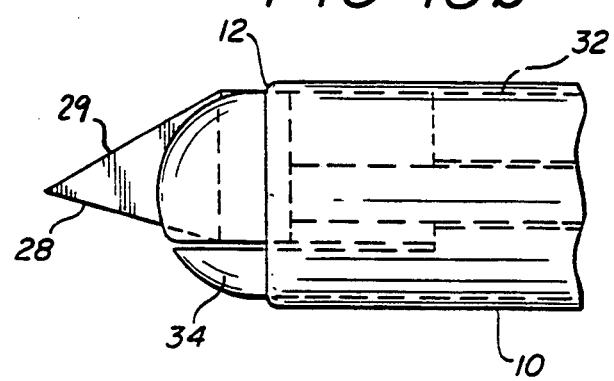

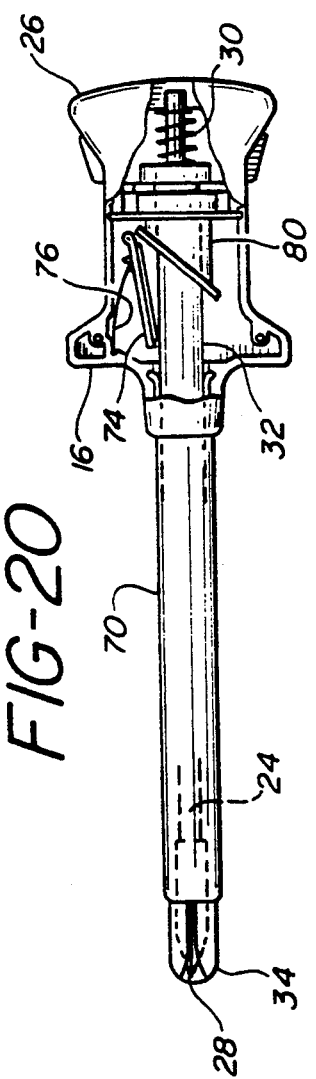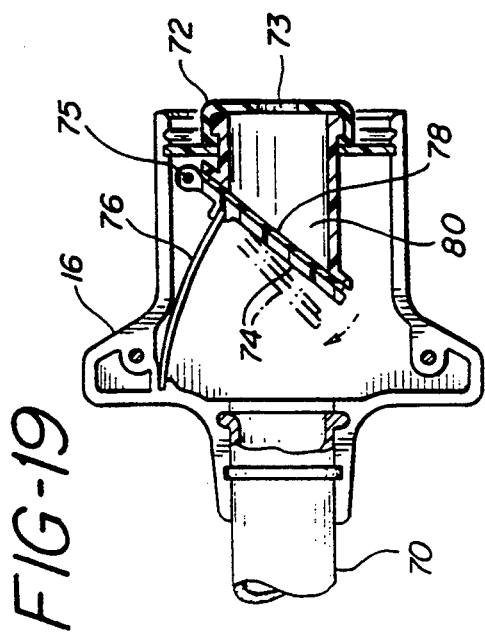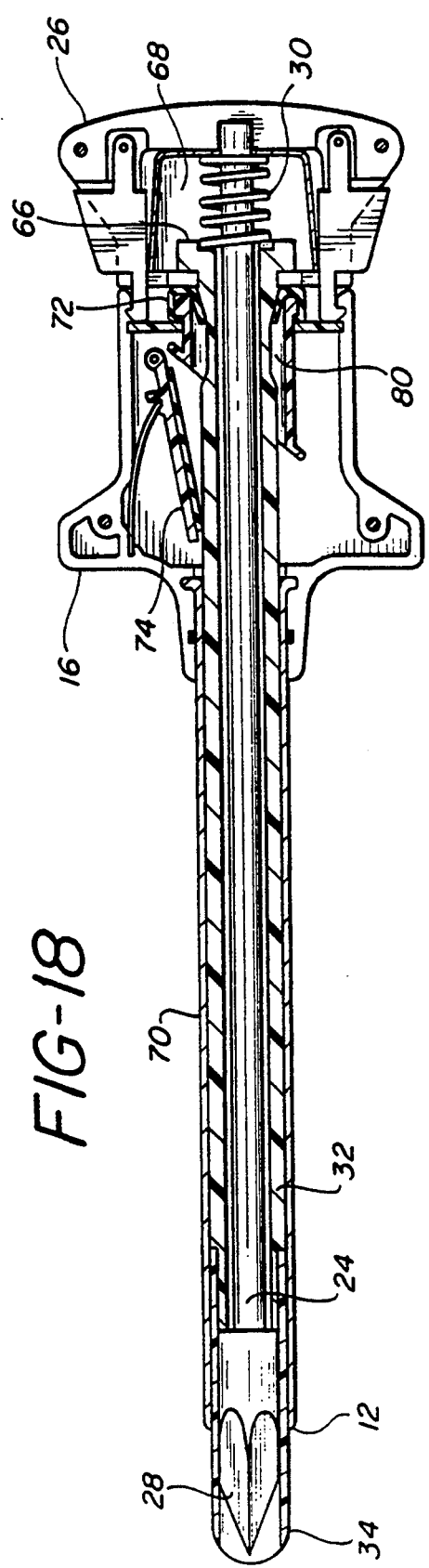

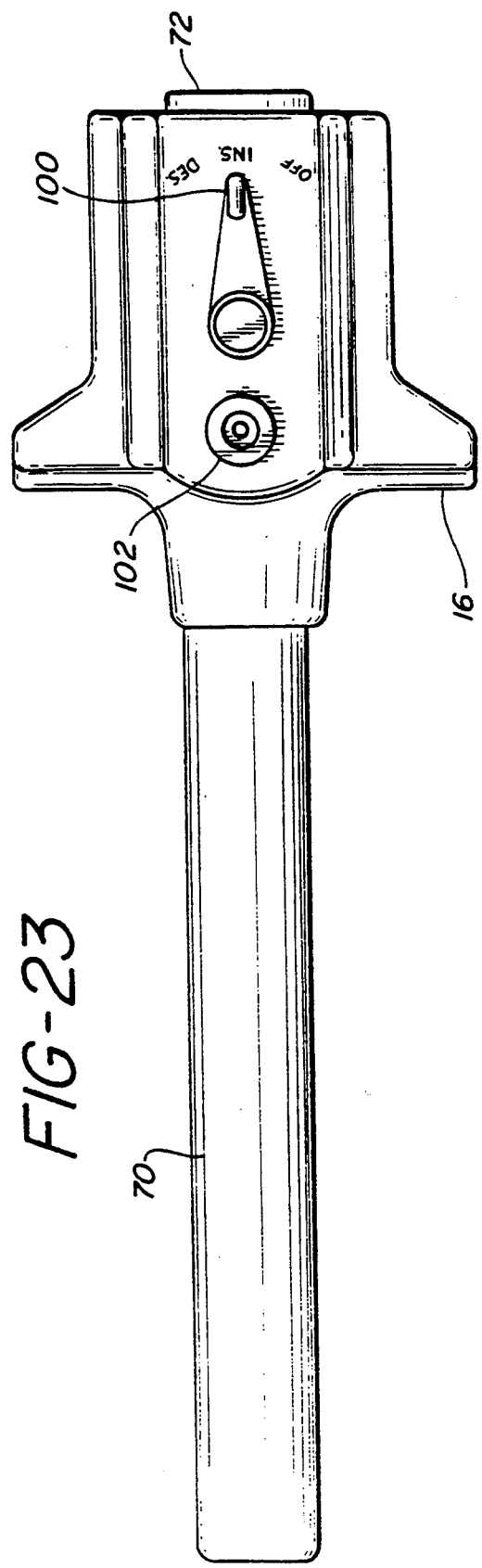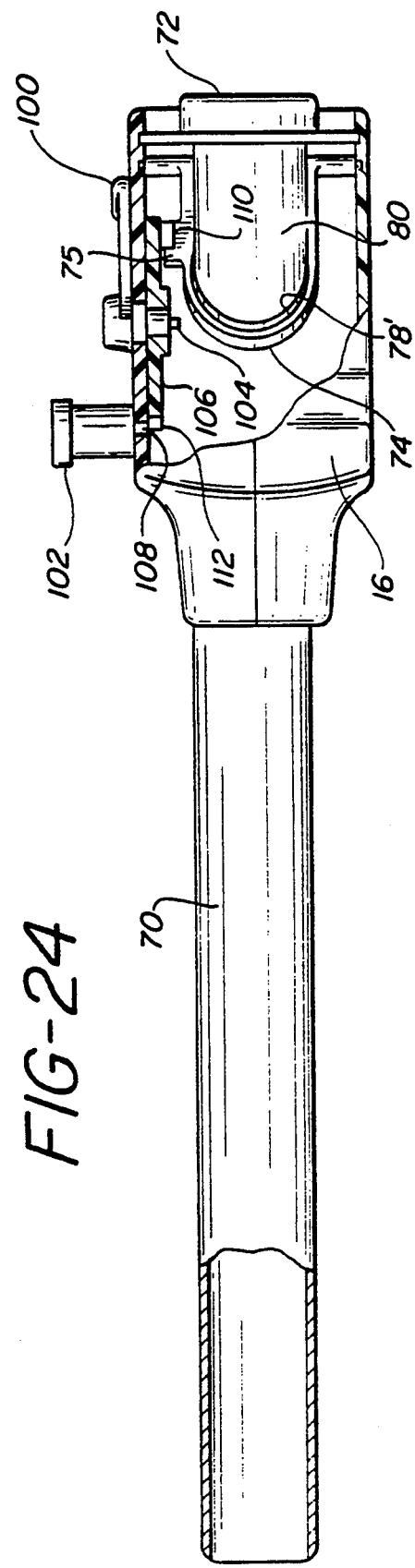

SAFETY TROCAR

This is a division of application Ser. No. 700,787, filed May 15, 1991, now U.S. Pat. No. 5,215,526, which is a continuation of Ser. No. 07/371,953, filed Jun. 27, 1989, now U.S. Pat. No. 5,066,288.

This invention relates to trocars used to puncture tissue for the performance of laparoscopic or arthroscopic surgery and, in particular, to such trocars which employ a safety device to shield the obturator point immediately after the point has perforated tissue.

A trocar generally comprises two major components, a trocar tube and an obturator. The trocar tube is inserted through the skin to access a body cavity through the tube in which laparoscopic or arthroscopic surgery is to be performed. In order to penetrate the skin, the distal end of the trocar tube is placed against the skin and an obturator is inserted through the tube. By pressing against the proximal end of the obturator the point of the obturator is forced through the skin until it enters the body cavity. At this time the trocar tube is inserted through the perforation made by the obturator and the obturator is withdrawn, leaving the trocar tube as an accessway to the body cavity.

It has been found that often a great deal of force is required to cause the obturator point to penetrate the skin and underlying tissue. When the point finally breaks through this tissue, resistance to penetration is suddenly removed, and the obturator point can suddenly penetrate to reach internal organs of the body, which may cause lacerations and other injury to the internal organs. To avert this danger to the patient, trocars have been developed which carry a spring-loaded tubular shield within the trocar tube and surrounding the obturator. The distal end of the shield will press against the skin as the obturator point penetrates the body until the obturator has formed a perforation with a diameter sufficient to allow the shield to pass through. At that time the resistance of the tissue to the spring-loaded shield is removed, and the shield will spring forward to extend into the body cavity, surrounding the point of the obturator. The shield thus protects the internal body organs from inadvertent contact with the point of the obturator. A trocar including such a safety shield is described in U.S. Pat. No. 4,535,773, for example.

The tubular shield in such a trocar will, however, require the incision formed by the obturator to extend to a considerable diameter before the resistance of the tissue pressure has been sufficiently decreased to allow the safety shield to spring forward. It is only when the incision attains the diameter of the shield that the shield is fully able to spring into the body cavity. When the obturator employs a long, tapered cutting tip, this tip must extend a significant distance into the body before the incision is sufficiently enlarged to release the safety shield. It would therefore be desirable to provide a safety shield which will spring forward to shield the obturator tip as soon as possible after entry is gained to the body cavity.

In accordance with the principles of the present invention, a safety shield for a trocar obturator is provided which exhibits a rounded, bullet-shaped distal end. A slot is formed in this distal end which corresponds to the geometry of the obturator tip, through which the tip extends during perforation of the skin. With this distal end conforming to the geometry of the tip, a smooth transition is provided from the tip to the distal end of the shield, enabling the shield to closely follow the obturator tip through the tissue. The rounded distal end will press against the skin and tissue in close proximity to the periphery of the incision as it is formed, and will aid in the enlargement of the incision to enable the shield to spring forward as soon as entry is gained into the body cavity.

It is desirable for the obturator to slide smoothly within the trocar tube during both insertion and retraction of the obturator. Opposing this desire is the need to form the obturator to be nearly the same diameter as the tube, so that the perforation will be the size of the tube. Thus, tolerances are generally tight between the outside diameter of the obturator and the inside diameter of the trocar tube. Further complication is provided by the valve at the proximal end of the trocar tube, which is needed to seal the proximal end during removal of the obturator when the trocar tube and body cavity are insufflated with gases. The valve, which generally takes the form of a hinged flap or trumpet valve, is spring-loaded to bear against the obturator, thereby assuring that the valve will close automatically upon withdrawal of the obturator of the tube. As the valve bears against the obturator it will frictionally disrupt the entry and withdrawal of the obturator, and at times can even jam and lock the obturator within the trocar tube.

In accordance with a further aspect of the present invention, the valve within the proximal end of the trocar tube is oriented at an acute angle with respect to the trocar tube when the valve is closed. Ease of entry of the obturator or any endoscopic instrument is afforded when the shielded tip of the obturator or instrument presses against the angularly disposed valve, and the angular orientation minimizes jamming of the obturator or instrument and valve within the trocar. In a preferred embodiment the valve is manually controllable in discrete positions for insufflation, desufflation, and valve closure in concert with the operation of a gas fitting.

Further patient safety would be provided by preventing the sudden extension of the obturator into the body cavity as the obturator tip fully penetrates the tissue. In accordance with yet another aspect of the present invention, means are provided which permits only incremental advancement of the obturator as tissue penetration proceeds. Such incremental advancement is provided by a ratchet or screw mechanism, for instance.

It would further be desirable to provide the safety of the trocar with the safety shield, but in a device which reduces the component complexity of the trocar and tube with the spring-loaded safety shield. In accordance with still another aspect of the present invention, the trocar tube is spring-loaded and employed as the safety shield. Thus, as the obturator point breaks through the tissue, the trocar tube will spring forward automatically into the body cavity, thereby providing shielding about the tip of the obturator.

In the drawings:

FIGS. 9–11b and 18 illustrate operation of a trocar with a bullet nosed shield;

FIGS. 13-15b illustrate operation of a trocar with a bullet nosed shield and a triangular-pointed obturator;

FIGS. 19-21 illustrate a trocar with an angularly disposed valve at the proximal end of the trocar tube;

FIGS. 23-26 illustrate a control on a trocar for regulating insufflation of the body.

Figure 1:
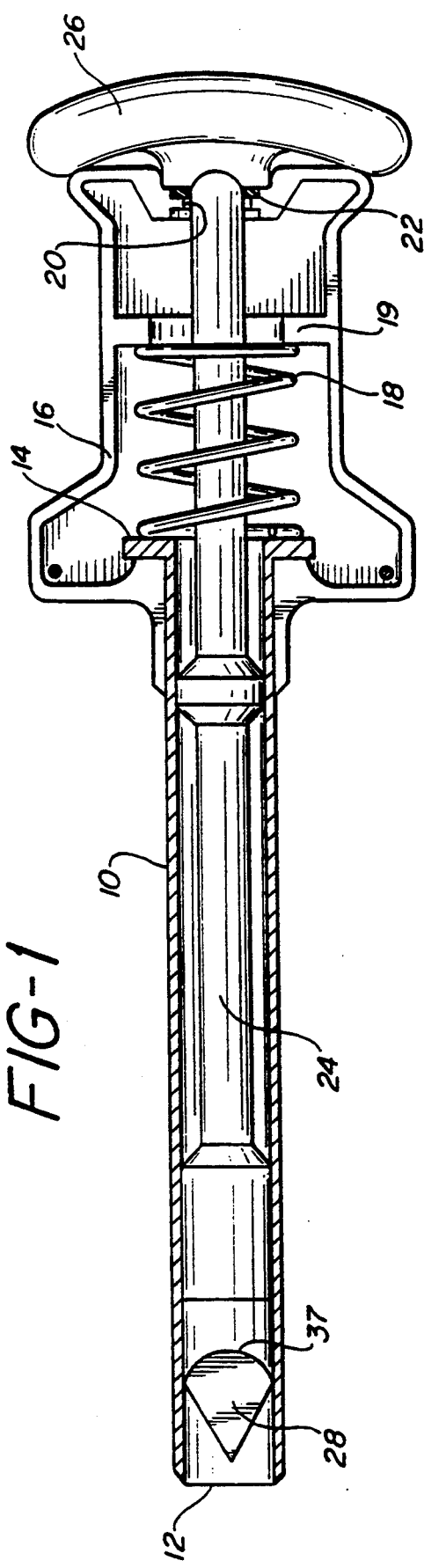
FIGS. 1–4 illustrate the use of the trocar tube to provide shielding of the obturator tip.

A safety trocar constructed in accordance with the principles of the present invention is shown in FIG. 1. The trocar includes a trocar tube or cannula 10 having an open distal end 12 and an open, flanged proximal end 14. The proximal end 14 is mounted in a trocar handle 16. A spring 18 is located inside the handle and abuts the flanged end of the trocar cannula 10 and a stop 19 within the handle 16. There is an aperture 20 at the proximal end of the handle 16 which is surrounded by a gasket ring 22.

Figure 2:
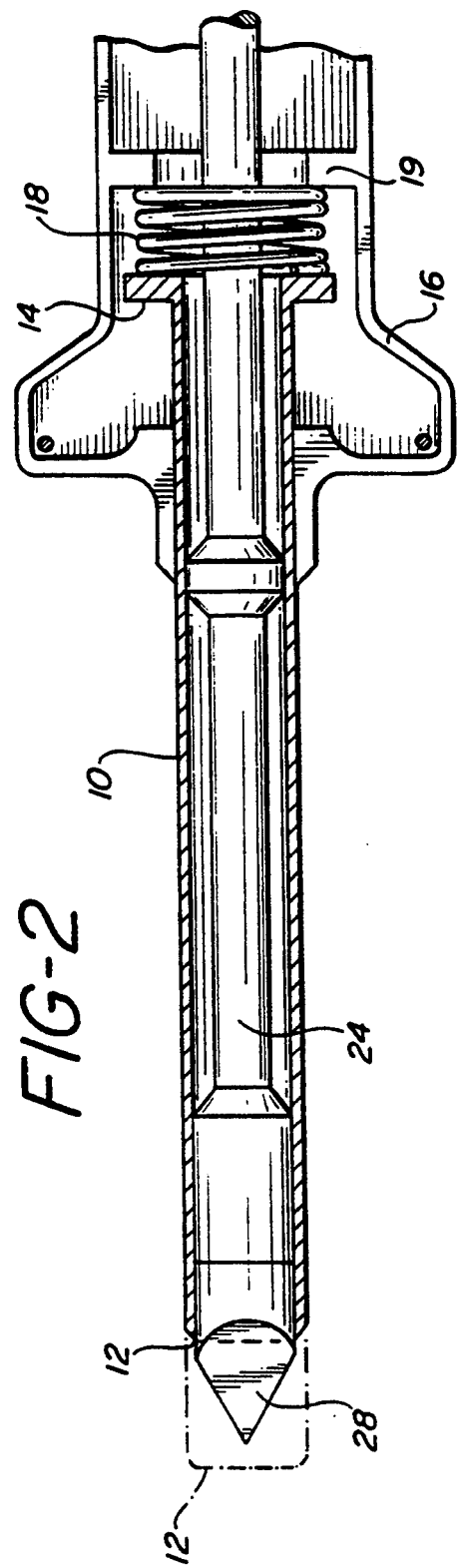

An obturator 24 is slideably and removeably located within the trocar cannula and is inserted into the handle and trocar cannula by way of the aperture 20. At its proximal end is an obturator handle 26, and the distal end of the obturator is sharpened to a point 28. The safety trocar of FIG. 1 is used to puncture a hole in soft tissue by placing the distal end 12 of the trocar cannula 10 against the tissue, and pressing against the obturator handle 26. As pressure is exerted against the obturator handle, the trocar cannula 10 begins to compress the spring 18 inside the trocar handle 16 and the trocar cannula retracts into the handle 16. This retraction of the trocar cannula exposes the obturator point 28, which punctures the tissue. FIG. 2 shows the spring 18 fully compressed within the trocar handle 16 and the obturator point 28 fully exposed beyond the distal end 12 of the trocar cannula. When the obturator point 28 breaks through the inner surface of the tissue, the spring-loaded trocar cannula 10 will spring forward around the obturator 24, shielding the obturator point to prevent inadvertent contact of the point with internal organs of the body inside the tissue being punctured.

Figure 3:
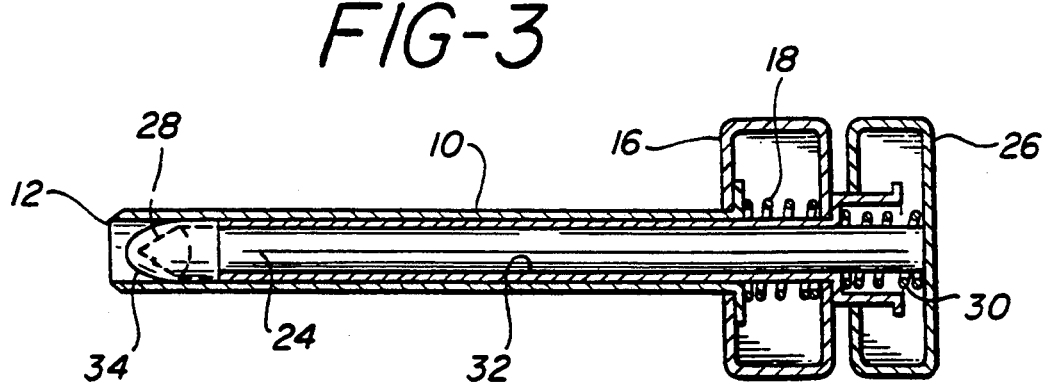
Figure 5A:
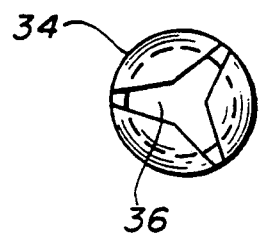
FIGS. 5a–8 illustrate a trocar safety shield with a bullet-shaped nose.

FIG. 3 shows a safety trocar in which like reference numerals refer to the elements previously described in FIG. 1. In FIG. 3 the obturator 24 is enclosed in a bullet nosed obturator shield 32. The obturator shield 32 is flanged at its proximal end to engage a spring 30 within the obturator handle 26. At its distal end the obturator shield has a slotted bullet-shaped nose 34. An end view of the bullet nose 34 is shown in FIG. 5a, with its slot 36. The slot 36 is seen to extend radially to the outer periphery of the bullet nose at the distal end of the obturator shield 32. In FIG. 3 the springs 18 and 30 are shown in their uncompressed positions.

Figure 4:
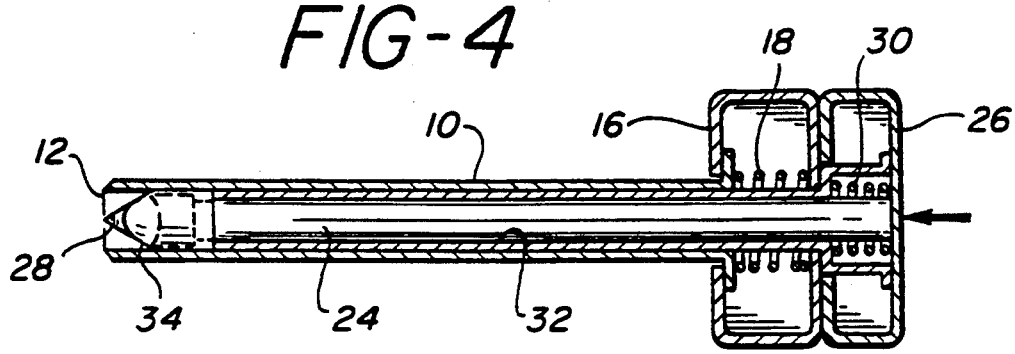
Figure 5B:
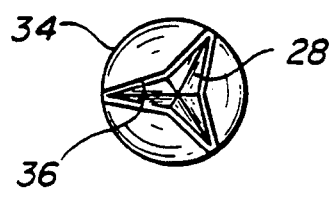

When pressure is initially exerted at the obturator handle 26, the spring 30 within the obturator handle compresses, as shown in FIG. 4. This compression of the spring 30 causes the obturator point 28 to extend beyond the bullet nose 34 of the shield through the slot 36, as shown in FIG. 5b. Further exertion of pressure at the handle 26 will cause the trocar cannula to compress the spring 18, and the obturator point will then begin to extend out the distal end 12 of the trocar cannula 10. The extended obturator point will then puncture the tissue at the distal end of the trocar cannula until the point breaks through the inner surface of the tissue. At that time the resistance at the distal end of the trocar will be removed, and the spring 18 will extend the trocar cannula 10 forward about the point 28 of the obturator. When the obturator and obturator handle are withdrawn from the trocar cannula, the bullet nosed shield will continue to protect the point of the obturator after it has been used. The spring-loaded trocar cannula 10 provides protection against accidental puncture of an organ within the body, and the shield 32 continues to provide protection against user injury after the obturator is withdrawn from the trocar cannula.

Figure 6:
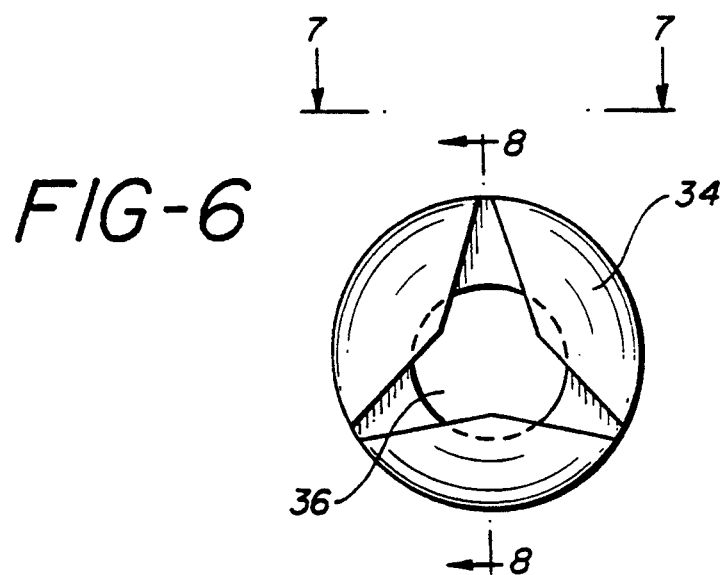
Figure 7:
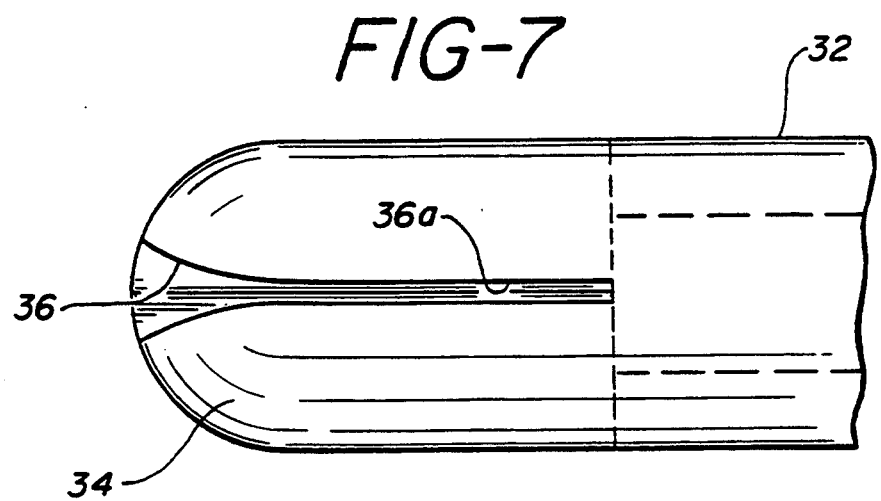
Figure 8:
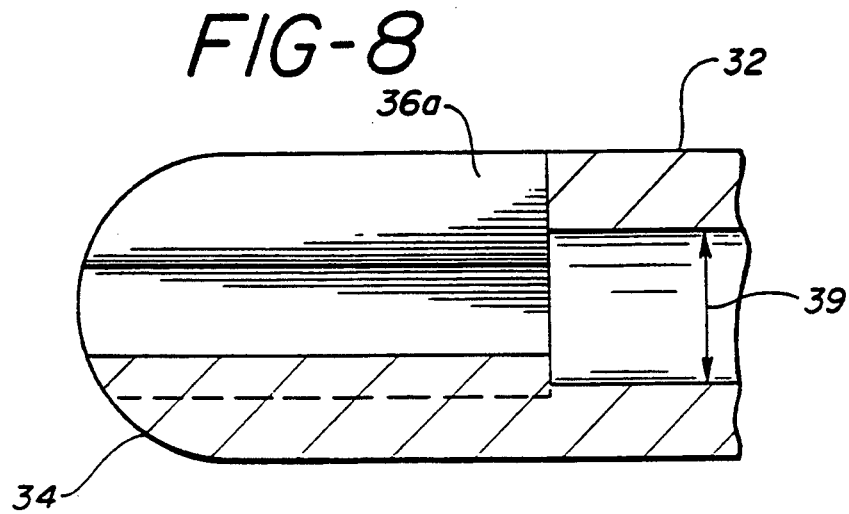

The bullet nosed end 34 of the shield 32 is shown in enlarged views in FIGS. 6-8. FIG. 6 shows an enlarged end view of the bullet nose 34 with a star-shaped slot 36. In the side view of FIG. 7, the slot 36 is seen to extend toward the rear of the shield as indicated at 36a. The sharpened edges of the star-shaped obturator point will thus extend radially through slots 36a to the outer perimeter of the shield, and will hence cut a puncture the same diameter as the outer diameter of the shield 32. When the puncture is the same size as the shield, the shield is enabled to readily spring forward to protect the point of the obturator as it breaks through the inner surface of the tissue. The cross-sectional view of the bullet nose 34 in FIG. 8 shows the rearward extension of the slot 36a in which the edges of the obturator point slide, and the widened inner diameter 39 within the shield proximal the nose for the shaft of the obturator. The bullet nose 34 of the shield aids penetration through the punctured tissue and improves the blending between the obturator facets and the cannula, thereby improving the responsiveness of the spring-loaded cannula.

Figure 9:
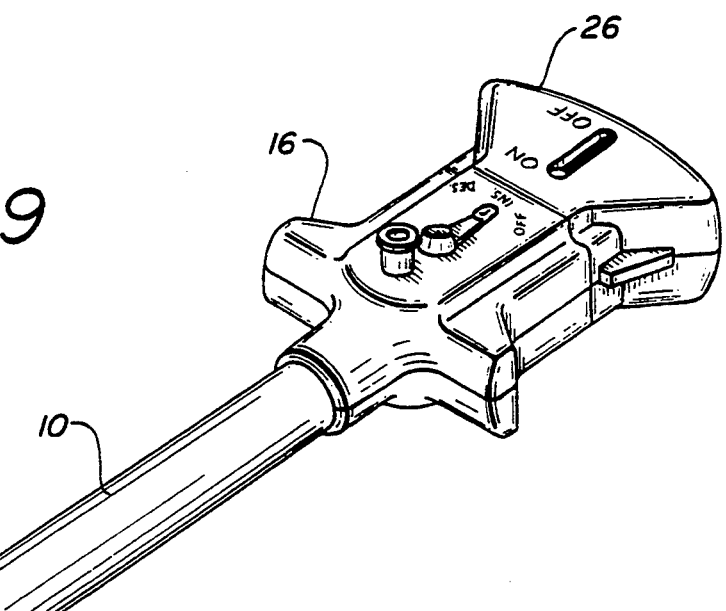
Figure 10:
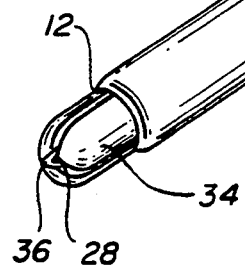
Figure 11A:
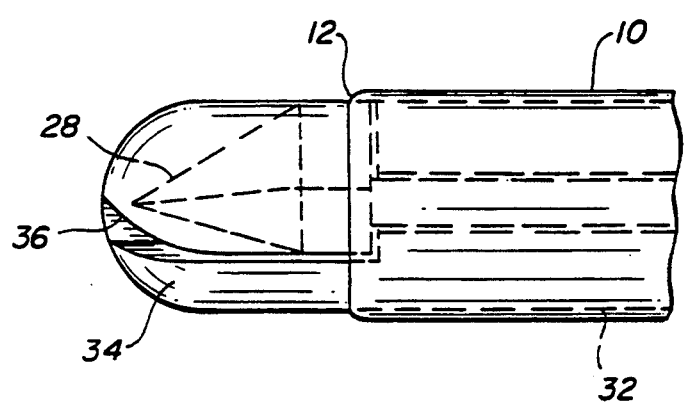
Figure 11B:
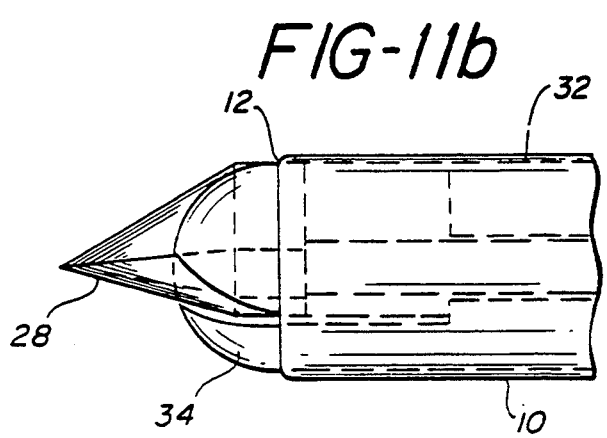

Operation of the trocar with bullet nosed shield of FIGS. 3-8 is shown in FIGS. 9-11. FIG. 9 is a perspective view of the trocar with the trocar cannula 10 compressed inside the trocar handle 16 so that the bullet nose 34 of the shield extends from the distal end 12 of the trocar cannula. An end view of the distal end of the instrument is shown in FIG. 10. FIG. 11a is an enlarged side view of the distal end of the instrument of FIG. 9, with the bullet nose 34 extended and the star-shaped obturator point 28 still retracted within the shield. In FIG. 11b the obturator point 28 is shown extended from the slot 36 of the bullet nose 34.

Figure 12A:
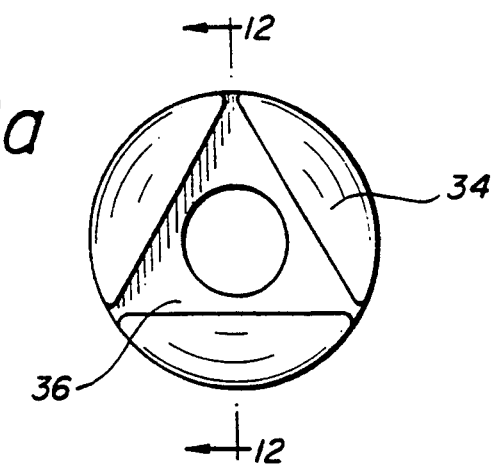
FIGS. 12–12d illustrate a bullet nosed safety shield when used with a triangular-pointed obturator.
Figure 12:
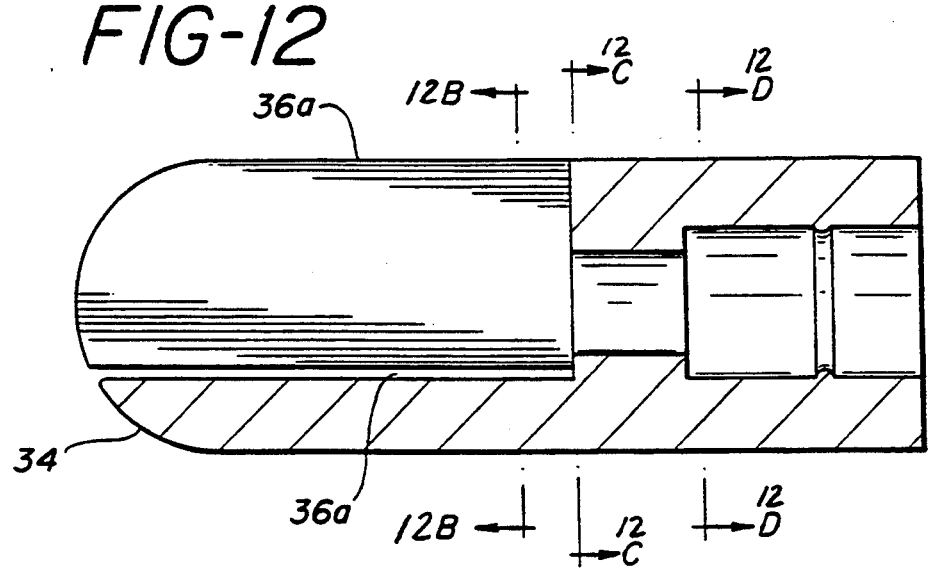
Figure 12B:
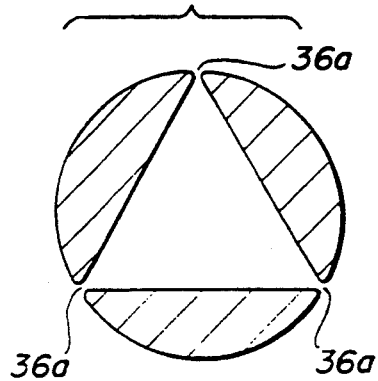
Figure 12C:
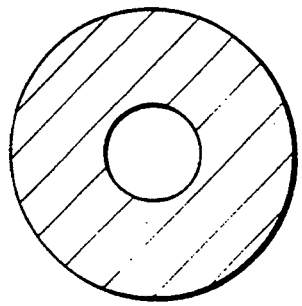
Figure 12D:
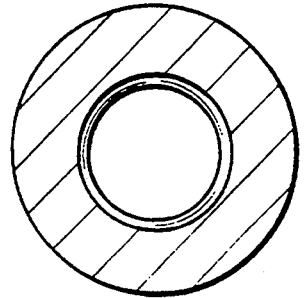

FIGS. 12-12d are similar to FIGS. 6-8, and show the bullet nose 34 of the shield 32 when used with a triangular-pointed obturator. FIG. 12 shows the bullet nose 34 in cross-section, with slot 36a extending along the side of the shield. FIG. 12a is a view of the distal end of the bullet nose, showing the triangular slot 36 extending to the periphery of the shield. FIGS. 12b, 12c, and 12d are cross-sectional views taken as indicated for areas B, C, and D of FIG. 12.

Operation of the trocar with a triangular pointed obturator is as shown in FIGS. 13-15b. FIG. 13 is a perspective view of the trocar, with the trocar cannula pressed into the handle 16 to reveal the bullet nose 34 of the shield at the distal end 12 of the trocar cannula. The indicator on the obturator handle is in the "on" position, indicating to the user that the obturator point 28 is retracted within the bullet nosed shield 32. FIG. 14 shows the distal end of the instrument and the triangular point 28 of the obturator within the triangular slot 36. FIG. 15a shows the bullet nose 34 of the shield 32 extending beyond the distal end 12 of the trocar cannula 10, with the obturator point 28 still within the bullet nose 34. FIG. 15b shows the obturator point 28 in its extended position. It may be seen that the edge 29 of the obturator point 28 is fully extended to the outer periphery of the bullet nosed shield 32 so as to cut a puncture of the same diameter as that of the shield. The three semi-circular fingers of the rounded bullet nose 34 will then fold the three opposing flaps of tissue aside as the shield 32 springs forward around the obturator point 28 when the puncture is made. In addition there is less trauma to the skin caused by pressing the rounded bullet nose fingers against the tissue as compared to the trauma caused by a tube-like shield.

Figure 28:
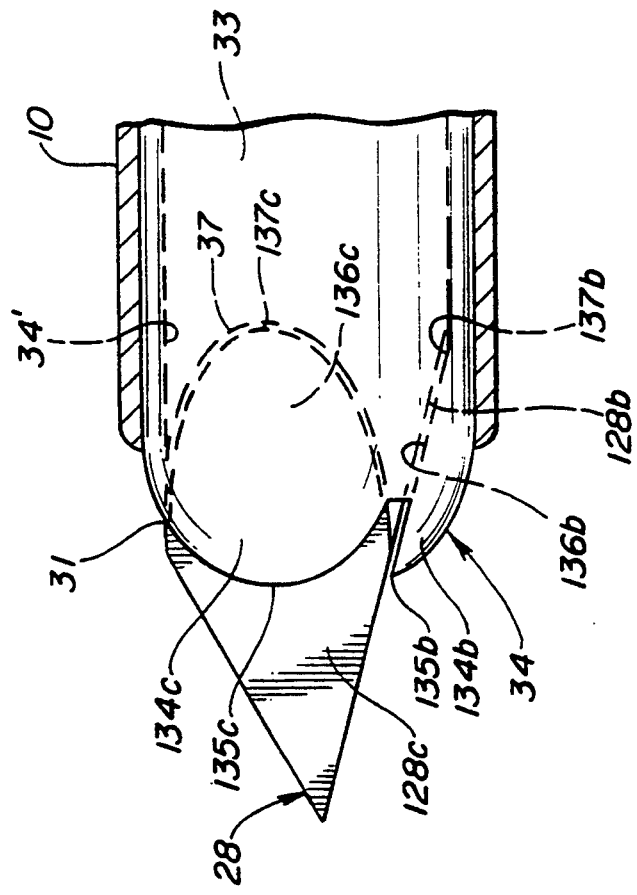
FIGS. 27 and 28 illustrate an obturator and shield combination which requires only a short extension of the obturator from the distal end of the shield.
Figure 27:
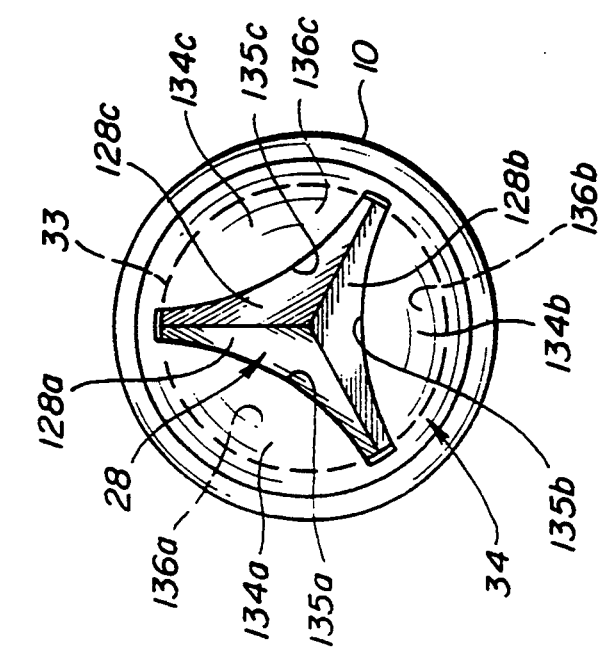

An embodiment of an obturator and shield which requires only a short extension of the obturator point is shown in FIGS. 27 and 28. In this embodiment there are no slots 36a extending along the sides of the shield from the end slot 36. Instead, the obturator point 28 cuts only to a radial dimension 31 at the outer edges of the point, within the inner diameter 34' of the shield. In prior art instruments which cut to this radius, the obturator point must be extended out of the shield to the blend 37 of the point 28 and the round shaft 33 of the obturator. In the illustrated embodiment, the obturator point 28 need be extended only half this distance from the bullet nosed shield 34 in order to achieve a cut of the full point diameter.

In the embodiment of FIGS. 27 and 28 the hemispheric bullet-shaped nose of the shield is seen to comprise three distal lobes, 134a, 134b, and 134c, each with a semicircular distal end 135a, 135b, and 135c which define the slot through which the obturator point 28 extends. The triangular pyramidal obturator tip 28 has three substantially flat surfaces or faces 128a, 128b, and 128c which are ground to blend into the cylindrical shaft 33 of the obturator as shown at 37. FIG. 28 shows that each lobe 134a, 134b, and 134c is thickened to have a substantially flat inner surface 136a, 136b, 136c, one of which is shown in this FIGURE. This inner surface contacts and fits against the proximal surface of the corresponding face of the obturator tip when the tip is fully extended, at which time the proximal edge 137a, 137b, 137c of each thickened lobe is substantially aligned with the blend 37 of each face. Thus, the geometry of the bullet-shaped nose is closely aligned with that of the obturator tip, and the lobes will fit against the faces of the tip and follow the tip into the perforation as it is cut by the tip. The lobes will spread the edges of the perforation to accommodate the bullet-nosed shield and the shield will then spring forward to protect the obturator tip as soon as the tip breaks through the tissue.

Figure 16:
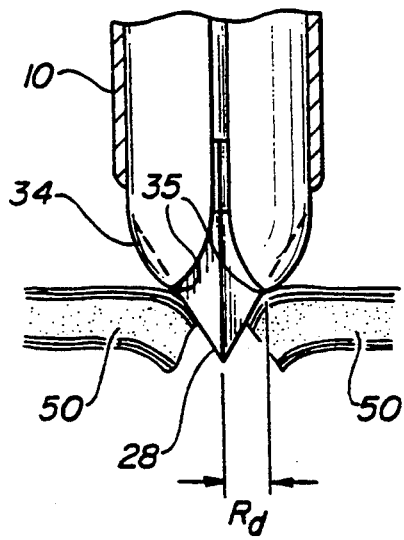
FIGS. 16 and 17 illustrate the penetration of tissue by a trocar with and without a bullet nosed safety shield.
Figure 17:
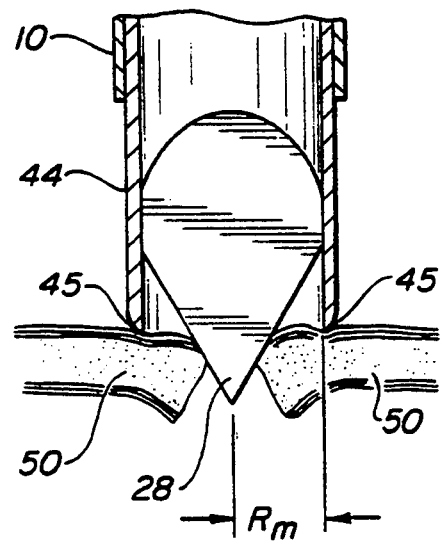

FIGS. 16 and 17 compare operation of the safety trocar of the present invention with that of prior instruments. Both FIGURES show trocars in operation just as the obturator tip breaks through the tissue 50. FIG. 17 illustrates operation of known instruments, in which the shield for the obturator point is a tubular shield 44. This shield engages the tissue being punctured as shown at 45. This shield is not able to overcome the tissue resistance at 45 and spring forward to protect the obturator point until the obturator has made a puncture with a radius as indicated by $R_m$. When this occurs, the obturator point 28 is already well within the body and may have already damaged organs inside the body. By comparison, the bullet nosed shield 34 contacts the tissue outside the puncture site at points indicated at 35 in FIG. 16. These contact points are at a much smaller radius $R_d$ from the obturator point 28. This smaller radius, together with the spherical shape of the nose 34, enable the bullet nosed shield to spring forward through the puncture at a much earlier time than the prior tubular shield, thereby protecting the point 28 of the obturator as soon as it breaks through the tissue.

By virtue of this superior protective action, a trocar can be made to rely solely on the protective action of the spring-loaded shield 32 without the spring-loaded trocar cannula. An embodiment of this type is shown in FIG. 18. The trocar cannula 70 is attached at its proximal end to the cannula handle 16. The obturator shield 32 and obturator 24 slide within the trocar cannula 70. A flange 66 at the proximal end of the shield 32 engages the spring 30, and is slideably engaged within a passageway 68 in the obturator handle 26. The bullet nose 34 of the shield is shown extended beyond the distal end 12 of the trocar cannula, but with the obturator point 28 still retracted within the shield. As the spring 30 is compressed when the bullet nose 34 contacts the tissue being punctured, the obturator point 28 will extend beyond the bullet nose and puncture the tissue. Once the point has broken through the tissue, the bullet nosed shield 32 will spring through the puncture to shield the point 28 within the body.

Figure 21:
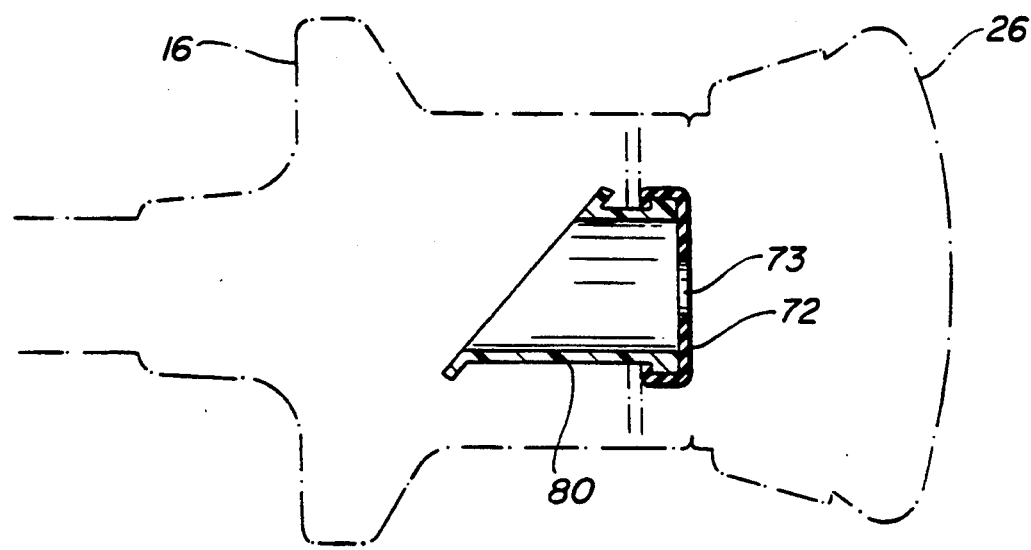

Prior to and after retraction of the obturator from the body, the body at the puncture site is generally insufflated with air. To prevent the air from escaping through the puncture, the trocar cannula and handle are generally equipped with a valve mechanism to prevent air leakage. FIG. 19 is a cross-sectional view of the trocar handle 16, showing a proximal tubular passageway 80 which is angled at its distal end. At the distal end of the passageway 80 is a flap valve 74 which is hinged at 75. A rubber-like sealing pad 78 is located on the side of the flap valve which contacts the distal end of the passageway 80. At the proximal end of the passageway 80 is a replaceable gasket 72 which has an aperture 73. The use of gaskets with different diameter apertures permits the trocar to be used with instruments of many different sizes. The internal diameter of the passageway 80 is sized to allow the shield 32 to smoothly slide through the passageway with the gasket 72 providing a seal around the shield. FIG. 21 shows an enlarged view of the trocar handle 16, the obturator handle 26, the passageway 80, and the gasket 72.

FIG. 20 shows the shield 32 and obturator 24 completely inserted within the trocar cannula 70. After the puncture is made, the shield 32 and obturator 24 are withdrawn from the trocar cannula 70, and the flap valve 74 swings shut against the distal end of the passageway 80 as the shield 32 clears the distal end of the passageway. The flap valve swings closed under the force of a spring 76. The distal end of the passageway 80 is thus securely sealed against air leakage while the shield is still sealing the proximal end of the passageway 80 at the gasket 72. The angled distal end of the passageway 80 permits the flap valve to be easily pushed open by the shield, or any endoscope instrument and prevents the shield from becoming jammed between the sealing pad 78 and the passageway as the flap valve closes. The distance between the flap valve 74 and the proximal gasket 72 ensures that the valve will be completely closed before the shield is removed from the gasket. Additionally the design of the trocar of FIG. 20 enables a user to selectively expose the obturator point or retract it into the shield.

Figure 22:
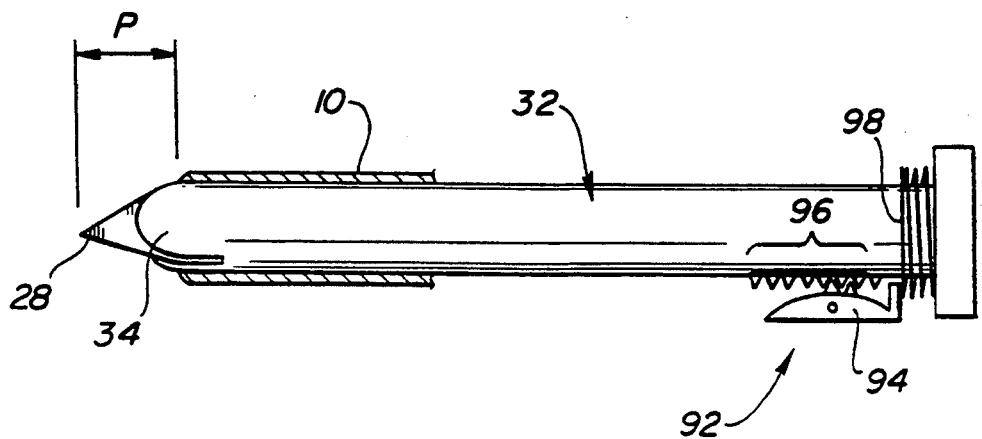
FIG. 22 illustrates apparatus for permitting only incremental advancement of the obturator of a trocar.

During some surgical procedures, a substantial amount of force is required to cause the obturator to puncture the tissue. The sudden release of back pressure as the puncture is achieved often causes the obturator to burst through the tissue and injure organs within the body. FIG. 22 shows a trocar which prevents this sudden breakthrough and extension into the body. The handle of FIG. 13 is adapted in a way to provide a ratchet mechanism as shown in FIG. 22. Located within the obturator handle 26 is a mechanism 92 connected to the obturator or shield 32 which permits only incremental advancement of the obturator. In FIG. 22 this mechanism 92 is illustrated as a pivoting toothed cam 94, which engages matching teeth 96 on the shield 32. A return spring 98 is connected to the proximal end of the cam 94 so that the mechanism 92 will exhibit a ratchet-like operation, permitting extension of the obturator in small incremental distances. The cam 94 extends into the slot of handle 26 described in FIG. 13, containing the "On" and "Off" markings, and can be actuated by the user, in such a way so as to move the cam 94 along the axis of the obturator shaft. The mechanism 92 permits the obturator to be extended only a total distance "P" into the body, which is sufficient to provide a puncture of the desired diameter. The ratchet mechanism 92 is only illustrative of the types of mechanisms that may be employed. Other suitable mechanisms include a linear or rotary double pawl clock escapement, or a coarse pitch screwing action whereby the obturator is incrementally advanced as the obturator handle is turned. Either these or other suitable mechanisms will permit only incremental advancement of the obturator while providing tactile feedback to the surgeon indicating that the obturator is being advanced through the tissue.

FIGS. 23–26 illustrate a control on the trocar handle for enabling regulation of the insufflation of the body. The control includes a pivotally mounted lever 100 located on the top of the trocar handle 16. The lever 100 is moveable to three discrete positions: off, insufflate, and desufflate. At a position just forward of the lever 100 is an insufflation fitting 102, located over a passageway 108 which leads to the interior of the handle 16. Connected to the pivot shaft 104 of the lever is a key 106, which pivots with the lever.

Figure 25:
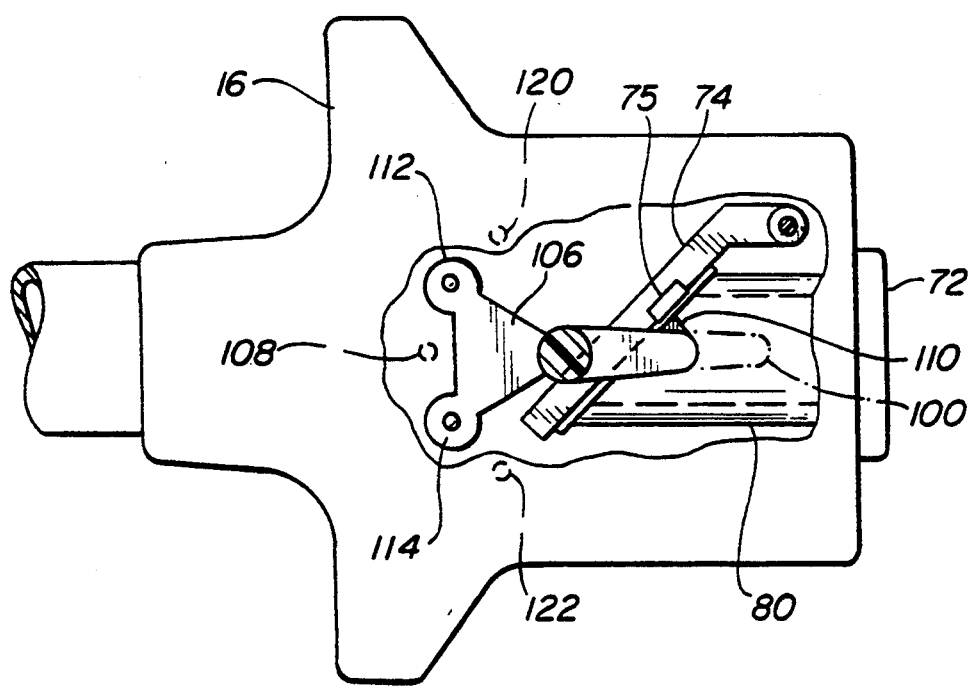

FIG. 25 is a plan view of the handle 16 with the top of the handle removed. In this view the key 106 is seen to have two ears 112 and 114, each with an upward extending central dimple. As the key is rotated with the lever, the dimples trace an arc along the top of the handle. Located in this arc of travel are the passageway 108 and two depressions 120 and 122, which act as detent positions for the dimples on the key ears 112 and 114. Located on the proximal extension of the key 106 is a pointer 110, which opposes an upward extension 75 of the flap valve 74 within the handle 16 (see FIG. 24). FIG. 24 illustrates that the angled distal end of the passageway 80 may have its own circular gasket 78' located around the distal end of the passageway.

When the lever 100 is rotated to the "off" position, the dimple on the key ear 112 clicks into the depression 120 and the dimple on the key ear 114 fits into the inner end of the insufflation passageway 108, thereby sealing the passageway. With the passageway 108 sealed, pressurized air inside the trocar cannula 70, the trocar handle 16 and the body will not leak out of the insufflation fitting. The flap valve 74 seals the distal end of the passageway 80 at this time.

Figure 26:
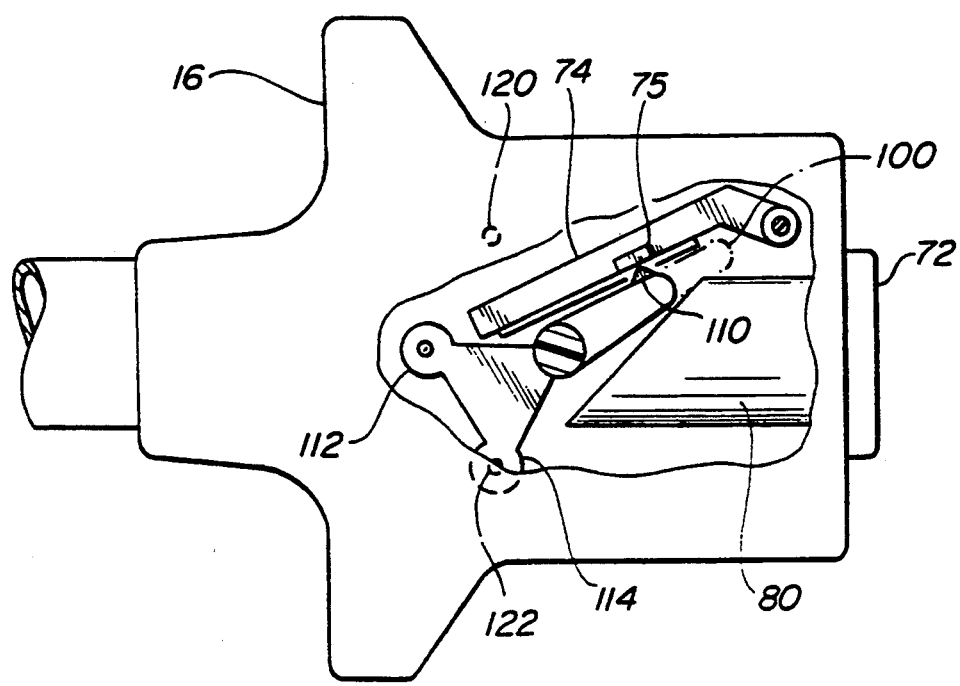

When it is desired to insufflate the body, a source of pressurized gas is connected to the insufflation fitting and the lever is moved to the "insufflate" position as shown in FIGS. 23, 24, and 25. In this position the passageway 108 is not blocked by the key 106 and pressurized gas may enter the interior of the handle and the trocar cannula through the insufflation fitting 102, insufflating the body. After the body has been properly insufflated with gas, the lever 100 may be moved back to the "off" position to seal the pressurized gas in the trocar, and the gas source may be removed from the fitting 102. When it is desired to desufflate the body, the lever 100 is pivoted to the "desufflate" position as shown in FIG. 26. The pivoting of the lever causes the key pointer 110 to contact the flap valve extension 75 and swing the flap valve away from its sealing position at the distal end of the passageway 80. Pressurized gas within the handle and trocar cannula will thus be vented through the passageway 80. As the key swings to its detent position the dimple on the key ear 114 clicks into the depression 122 and the dimple on the key ear 112 seals the passageway 108 to prevent the venting of air through the passageway 108 and the insufflation fitting 102.

What is claimed is:
1. A trocar containing:
    a cannula attached to a cannula handle;
    an obturator attached to an obturator handle, said obturator covered by a safety shield reciprocable within said obturator handle, said safety shield urged distally in said obturator handle by a spring mechanism;
    a movable latching mechanism located partly on said obturator handle and partly on said cannula handle, said latching mechanism capable of releasably engaging said obturator handle to said cannula handle, upon insertion of said obturator into said cannula handle such that the engagement of said handles actuate said safety shield to allow said obturator to be exposed from the distal end of said safety shield.

* * * * *